United States Patent [19]

Foster et al.

[11] Patent Number: 5,616,324

[45] Date of Patent: Apr. 1, 1997

[54] PRO-INFLAMMATORY COMPOSITION COMPRISING AT LEAST TWO MEMBERS OF THE GROUP CONSISTING OF DL. PHENYLALANINE, RUTA GRAVEOLANS AND CORYDALIS BULBOSDA

[76] Inventors: Antoinette Foster, 10 Chambers Road, Bunyip, Victoria, 3815, Australia; Don Foster, "Glen Luce", Brookdale Avenue, Emerald, Victoria 3782, Australia

[21] Appl. No.: 456,091

[22] Filed: May 31, 1995

[51] Int. Cl.$^6$ ..................................... A61K 35/78
[52] U.S. Cl. ................. 424/195.1; 424/601; 424/602; 424/606; 424/675; 424/679; 424/696; 424/709; 514/345; 514/356; 514/557; 514/778; 514/825; 514/886
[58] Field of Search ..................... 424/195.1, 601, 424/602, 606, 709, 679, 696, 675; 514/356, 345, 557, 770, 886, 825

[56] References Cited

U.S. PATENT DOCUMENTS

| | | | |
|---|---|---|---|
| 3,843,788 | 10/1974 | Iwasa, et al. | 424/195.1 |
| 4,439,452 | 3/1984 | Ehrenpreis et al. | 514/561 |
| 5,013,553 | 5/1991 | Southard et al. | 424/426 |

*Primary Examiner*—John W. Rollins
*Attorney, Agent, or Firm*—Edwin D. Schindler

[57] ABSTRACT

A synergistic mixture particularly suitable for the treatment of animals whic consists of at least two of the group consisting of DL.Phenylalanine, Ruta Graveolans and Corydali Bulbosa together with a carrier to make up a required volume, the mixture having a pro-inflammatory effect which accelerates the healing process of inflammation. It is preferred that there is provided mixture of DL.Phenylalanine with one product selected from the group of Ruta Graveolans and Corydalis Bulbosa. In a specific form, the mixture also includes Nicotinic Acid.

9 Claims, No Drawings

PRO-INFLAMMATORY COMPOSITION COMPRISING AT LEAST TWO MEMBERS OF THE GROUP CONSISTING OF DL. PHENYLALANINE, RUTA GRAVEOLANS AND CORYDALIS BULBOSDA

This invention relates to a pro-inflammatory synergistic mixture to accelerate healing of inflammatory conditions and in particular for use with animals, such as horses.

Pharmaceutically an anti-inflammatory drug blocks the inflammatory healing symptoms by suppressing prostaglandins and leukotrienes, the body chemicals which bring about inflammation as a response to injury, infection and allergens.

There have of course been previously proposed many anti-inflammatories and pain relieving medications which have been more or less successful and some of which have greater or less side effects. The process of inflammation (pain, swelling, fever, redness and loss of function) is however necessary for healing but becomes a problem when it is prolonged and ineffectual.

The object of the invention is to provide a pro-inflammatory mixture which accelerates, facilitates and shortens the inflammatory progress and which uses natural products which appear to have a strong synergistic effect and which provide a product which has shown, in practise, to have extremely effective results with no side effects. This synergistic mixture accelerates the healing process of inflammation by providing boosted levels of those natural minerals and vitamins which are present in inflamed tissues but often at insufficient levels to afford rapid healing.

The invention in its broadest sense comprises a synergistic mixture of at least two of the group consisting of DL.Phenylalanine, Ruta Graveolans and Corydalis Bulbosa together with a carrier to make up a required volume, the mixture having a pro-inflammatory effect which accelerates the healing process of inflammation.

In a preferred form of the invention we provide a mixture of DL.Phenylalanine with one product selected from the group of Ruta Graveolans and Corydalis Bulbosa.

It may be preferred that the mixture also includes Nicotinic Acid.

In order that the invention may be more readily understood, we shall describe certain embodiments of the invention, together with possible variations thereof.

A preferred formula which we have developed is:

| INGREDIENT | % BY WEIGHT |
|---|---|
| DL. Phenylalanine (an amino acid) | 12 |
| Nicotinic Acid (VB3) | 4 |
| Ca Pantothenate (VB5) | 4 |
| Pyridoxine HCl (VB6) | 1 |
| Ruta Graveolans (RUE - European herb) | 10 |
| Corydalis Bulbosa (Chinese herb) | 10 |
| Mineral Mixture (12 mineral mix-see below) | 24 |
| Skim Milk Powder | 18 |
| Soy Bean Powder | 17 |

The mineral mixture referred to may, in a preferred form comprise:

| MINERAL MIXTURE CONTENTS | % BY WEIGHT |
|---|---|
| Calcium Phosphate | 12 |
| Potassium Phosphate | 5 |
| Iron Phosphate | 5 |
| Monosodium Phosphate | 2.5 |
| Zinc Sulphate | 2.5 |
| Silica | 1.5 |
| Magnesium Phosphate | 7 |
| Potassium Chloride | 5 |
| Sodium Sulphate | 5 |
| Trisodium Phosphate | 2.5 |
| Calcium Sulphate | 1.5 |
| Calcium Fluoride | 0.3 |
| Combined with: | |
| King Island Kelp | 20 |
| Brewers Yeast | 18 |
| Wheat Germ | 15.2 |

In using this particular formulation, we have had exceptionally good results when used on horses having inflammation or pain and the normal method of delivery is to add the formulation to the horses food.

The preferred quantity given is of the order of 25 g mixed into the dry feed and this can be repeated once or twice a day, depending on the seriousness of the infection.

It is to be understood that the exact quantities of the ingredients used in the mixture which constitutes this invention are not pertinent to the invention except that at least two of DL.Phenylalanine, Ruta Graveolans and Corydalis Bulbosa must be included.

We have had horses with a high degree of inflammation and the use of the synergistic mixture of the invention has most surprisingly substantially reduced or completely overcome the inflammation in a very short period, on occasions in as little as 24 hours.

From field trials so far conducted, there have been no discernible side effects from the use of the formulation and such field trial results are currently proceeding.

The following are the results of four specific trials carried out by a Veterinary Surgical practice in Melbourne:

CASE 1.

A 12 year old thoroughbred horse doing advanced/Prix St. George dressage developed early ringbone in the near fore pastern joint. Treatment with rolled toe shoes and ingestion of the toe mixture of the formula in the quantities as set out herein enabled the horse to be ridden in five events for the following year before retirement.

CASE 2.

Seven year old thoroughbred horse doing novice elementary dressage with lumbar muscle pain on the off side. The diagnosis was subluxation of the dorsal spinous processes of the third and fourth lumbar vertebrae to the right, with associated longissimus dorsi muscle soreness on the off side. Veterinary manipulation to adjust the fixation back to the midline, along with treatment by use of the mixture enabled:the horse to be put back into full work.

CASE 3.

Four year old thoroughbred hunter/Jumper with blunt trauma (blunt bolt three inches long) up through the bars area of the near hind hoof through into the navicular bursa. Intravenous antibiotics, poulticing and the mixture: having the formula set out hereinbefore were used. Due to the long term need for anti-inflammatories and analgesics, phenylbutazone could not be used. The mixture of the formula enabled a satisfactory result over a three month period after which the horse was put back into work with no lameness.

A moderate swelling of the heel and pastern area of the hoof was still evident.

CASE 4

Six week old foal with extensive lacerations to the off hind cannon and fetlock. The mixture of the formula was used successfully to help reduce the swelling and inflammation and the wound healed well in four weeks.

Whilst the particular formula given is the one that has been preferred we believe that the main synergistic agents are the DL.Phenylalanine, which is an amino acid and Ruta Graveolans which is Rue, a European herb, and Corydalis Bulbosa, which is a Chinese herb.

It appears that a synergistic effect is achieved from any combination of two of these three components but, again, further field work is being carried out to ascertain the most desirable combination, and the proportions in such combinations.

The Nicotinic Acid also appears to assist in the effectiveness of the mixture.

The mineral formulation set out is one which is generally beneficial, particularly should there be some lack in the normal diet of some of the components of this but it is believed that, generally, the Iron Phosphate, the Silica and the Calcium Fluoride are those which are most beneficial. At the present time we have not fully quantified this.

It will be appreciated that, whilst the various formulations given herein are indicative of and are exemplifications of the invention, there may be modifications, particularly in the relative proportions of these and such modifications are deemed to be within the scope of the present invention.

We claim:

1. A composition having a pro-inflammatory effect which accelerates the healing process of inflammation, comprising:

a mixture containing at least two ingredients selected from the group consisting of DL.phenylalanine, ruta graveolans and corydalis bulbosa; and, a carrier for said mixture.

2. The composition according to claim 1, wherein said mixture includes DL.phenylalanine as one of said ingredients.

3. The composition according to claim 1, further comprising nicotinic acid.

4. The composition according to claim 1, further comprising a member selected from the group consisting of calcium pantothenate, pyridoxine hydrochloride, a mineral mixture and a combination thereof.

5. The composition according to claim 4, wherein said mineral mixture comprises a member selected from the group consisting of calcium phosphate, potassium phosphate, iron phosphate, monosodium phosphate, trisodium phosphate, magnesium phosphate, zinc sulfate, silica, potassium chloride, sodium sulfate, calcium sulfate, calcium fluoride and a combination thereof.

6. The composition according to claim 5, wherein said mineral mixture includes phosphate, silica and calcium fluoride.

7. The composition according to claim 4, wherein said mineral mixture is mixed with a member of the group consisting of Brewers Yeast, wheat germ, King Island kelp and a combination thereof.

8. The composition according to claim 1, wherein said carrier is selected from a member of the group consisting of skim milk powder, soy bean powder and a combination thereof.

9. The composition according to claim 1, further comprising an animal feed mixture for an oral administration of said composition to animals.

* * * * *